United States Patent [19]
Hutchins

[11] Patent Number: 5,236,600
[45] Date of Patent: Aug. 17, 1993

[54] PROCESS FOR CONTROLLING BACTERIA GROWTH IN WATER SUPPLY SYSTEMS

[76] Inventor: Danny T. Hutchins, 1065 Great Oaks, Rochester, Mich. 48307

[21] Appl. No.: 710,581

[22] Filed: Jun. 5, 1991

[51] Int. Cl.⁵ .............................................. C02F 1/50
[52] U.S. Cl. .................................. 210/739; 210/754; 210/764; 422/14; 422/28
[58] Field of Search ............... 210/752, 754, 764, 766, 210/739; 422/18, 28, 14

[56] References Cited

U.S. PATENT DOCUMENTS

| | | | |
|---|---|---|---|
| 4,056,470 | 11/1977 | Carpenter | 210/754 |
| 4,057,648 | 11/1977 | Hool et al. | 424/341 |
| 4,111,844 | 9/1978 | Polony et al. | 252/106 |
| 4,297,224 | 10/1981 | Macchiarolo et al. | 210/755 |
| 4,468,332 | 8/1984 | Peacock et al. | 210/755 |
| 4,472,187 | 9/1984 | Wojtowicz | 71/67 |
| 4,510,068 | 4/1985 | Rohlfs et al. | 252/186.29 |
| 4,545,956 | 10/1985 | Ciszewski et al. | 422/28 |
| 4,584,106 | 4/1986 | Held | 210/754 |
| 4,659,359 | 4/1987 | Lorenz et al. | 71/67 |
| 4,693,832 | 9/1987 | Hurst | 210/756 |
| 4,724,079 | 2/1988 | Sale et al. | 210/638 |
| 4,732,689 | 3/1988 | Harvey et al. | 210/754 |
| 4,741,833 | 5/1988 | Sheikh | 210/665 |
| 4,800,082 | 1/1989 | Karbowski et al. | 424/409 |
| 4,804,478 | 2/1989 | Tamir | 210/754 |
| 4,824,572 | 4/1989 | Scott | 210/602 |
| 4,846,979 | 7/1989 | Hamilton | 210/754 |
| 4,874,526 | 11/1989 | Grade et al. | 210/697 |
| 4,880,547 | 11/1989 | Etani | 210/728 |
| 4,986,902 | 1/1991 | Serna | 210/754 |

Primary Examiner—Ivars Cintins
Attorney, Agent, or Firm—Dykema Gosset

[57] ABSTRACT

A method and system is disclosed for adding chlorine to a water supply system to kill bacteria, and in particular, Legionella bacteria. A corrosion inhibitor additive is added with the chlorine, to ensure that corrosion or other damage to the pipes does not occur. A method is disclosed for initially setting up proper levels of chlorine and corrosion inhibitor, and maintaining those levels. Systems for adding the materials to the hot water supply system are disclosed to ensure that they are adequately and thoroughly mixed into the water.

12 Claims, 1 Drawing Sheet

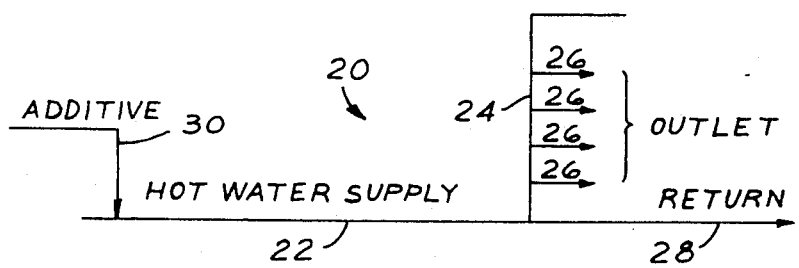
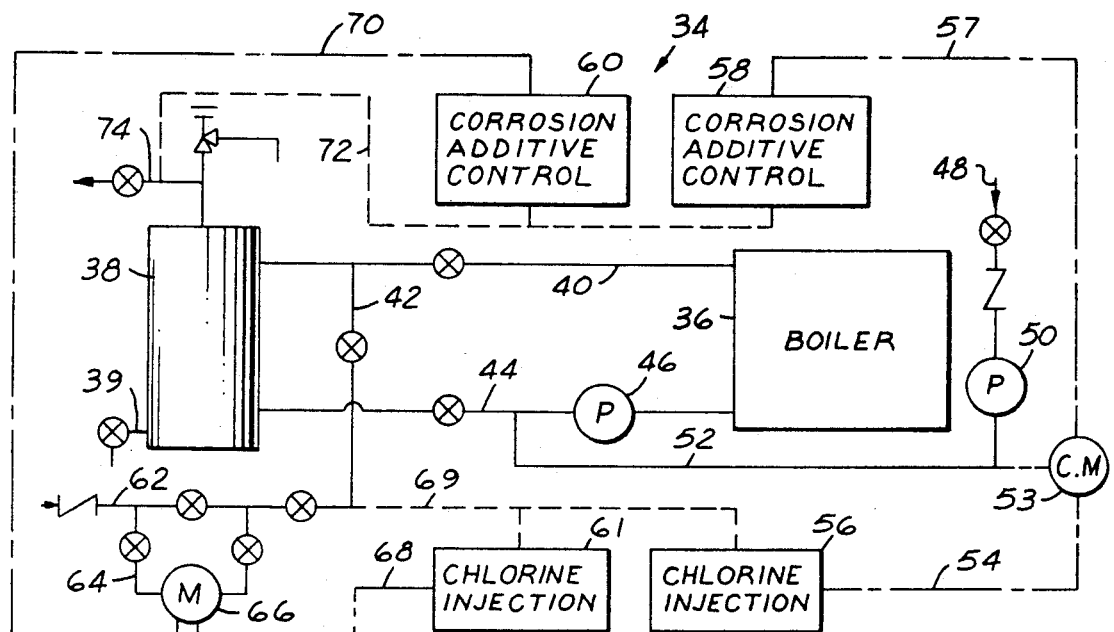
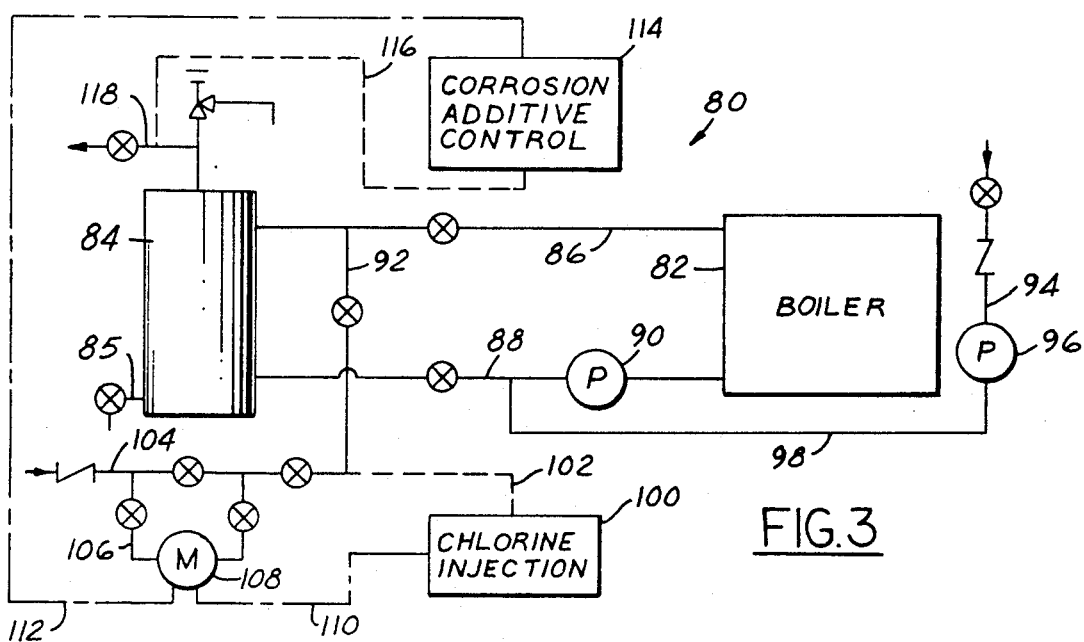

PROCESS FOR CONTROLLING BACTERIA GROWTH IN WATER SUPPLY SYSTEMS

BACKGROUND OF THE INVENTION

This application relates to a method of sterilizing water supply systems to eliminate bacteria, and then maintaining additives in the system to ensure bacteria growth does not reoccur.

Water supply systems are often exposed to dangerous bacterial growth. Several types of bacteria are naturally present in water and breed in low temperature hot water systems such as those commonly found in hospitals, schools, offices, or other publicly used buildings. One such bacteria type is the Legionella organism, which can cause Legionnaires disease. Legionnaires disease strikes up to 25,000 people each year in the United Stats. Evidence has indicated that Legionnaires disease is often spread through hot water supply systems in large public buildings.

Processes have been developed to effectively clean water supply systems in an inexpensive and effective manner. One such process adds chlorine to the water supply system, killing the bacteria. Such a process has proven effective in controlling the growth of Legionella, however, there are drawbacks to such a process. One main drawback is that the use of chlorine potentially corrodes and damages pipes. As such, some prior art processes have utilized chlorine in combination with corrosion inhibitors. One such process is disclosed in U.S. Pat. No. 4,468,332.

Further, the process of treating water with chlorine and an corrosion inhibitor additive such as a silicate, is known. Such a process is disclosed in U.S. Pat. No. 4,874,526.

The known prior art processes have not disclosed a system which is incorporated into a water supply system in a large public building. Further, such known methods do not disclose a treatment process for initially setting up, disinfecting and maintaining the disinfectant within the water supply system. Chlorine is not stabile in hot water, and thus the amount of chlorine in the hot water will decrease with time. It is therefore an object of the present invention to disclose a complete system and method for disinfecting the hot water supply systems of large buildings and maintaining desired levels of chlorine in the system.

SUMMARY OF THE INVENTION

In a disclosed method, a water supply system in a large building is disinfected by adding liquid sodium hypochlorite, or chlorine, and a corrosion inhibitor, preferably a silicate, to the hot water supply system.

In a first stage, the water supply system is studied. Data is accumulated indicating the level of several materials in water samples taken from outlets of the water supply system. This data is utilized to determine preferred chlorine levels for the water treatment.

Samples taken from all monitored sites are tested for the level of Legionella, total bacteria, water temperature and corrosion indicators such as iron, zinc and copper. The outlet samples are utilized to determine desired levels for the additives to be contained in subsequent treatment processes.

Once preferred levels have been identified, an injection system is incorporated into the hot water supply system, and chlorine and a corrosion inhibitor are added to the water supply. All system outlets are flushed such that all lines and points within the system are exposed to chlorine.

Next, a high dosage disinfectant stage may be performed which lasts approximately one week. High dosages of chlorine and a corrosion inhibitor are added to the water. All outlets and fixtures are flushed to ensure that the chlorine extends to all areas of the water supply system. Chlorine levels in the water are tested at various outlets to ensure that adequate flow of the additives is provided to all areas within the water supply system.

All problem areas are closely monitored. Such problem areas could include patient care areas in hospitals, and in particular critical care areas such as a bone marrow transplant area. Any areas under reconstruction are also closely monitored. Fixtures at the far end of the system, which are potential stagnant areas, are closely monitored. The hot water storage tanks and return lines are closely monitored. The monitored areas are tested for the levels of the above-listed materials. All monitored areas that do not have a desired chlorine and corrosion inhibitor level are recorded for later investigation and corrective action.

After the high dosage stage achieves a desired chlorine level, a moderate dosage disinfectant stage is performed which lasts approximately five weeks. The level of chlorine and corrosion inhibitors may be somewhat reduced. The addition of the additives is continued, and continued sampling of various outlets is performed. As an example, if this period lasts for five weeks, one fifth of the outlets may be tested each week. The sampling would be as described above. After the end of the maintenance period, all outlets are tested to ensure that bacteria levels and corrosion indicators are as desired.

Finally, an ongoing maintenance stage is initiated. Chlorine and corrosion inhibitor injection is continued at relatively low levels. Problem areas are periodically flushed to ensure that those areas are exposed to chlorine. The fixtures are tested periodically to determine that the chlorine levels are as desired, and that bacteria growth does not reoccur.

These and other objects and features of the present invention can be best understood from the following specification and drawings in which the following is a brief description.

BRIEF DESCRIPTION OF THE DRAWINGS

FIG. 1 is a highly schematic view of a water supply system incorporating the additive system of the present invention.

FIG. 2 is a largely schematic view of a circuit for injecting additives to the water supply system.

FIG. 3 is a largely schematic view of a second embodiment circuit for injecting additives to the water supply system.

DETAILED DESCRIPTION OF THE PREFERRED EMBODIMENT

Hot water supply system 20 is illustrated in FIG. 1 including hot water supply 22 leading to outlet line 24 which communicates with a plurality of outlets 26. Supply system 20 could be the hot water supply system for a large public building and there could be thousands of outlets 26. Return line 28 leads back to an inlet for hot water supply 22. In the method according to the present invention additives are added through line 30. The additives could include chlorine and a corrosion inhibitor, with the chlorine eliminating bacteria growth within the hot water supply system.

In a preferred method the additive levels for injection through line 30 are determined by intially making a preliminary investigation of the water supply system 20. An operator studies the water supply system, the plumbing design and blueprints and becomes familiar with the design and utilization of the building's water supply system. Water samples are taken to establish a reference base giving an indication of the level of bacteria problem within water supply system 20.

This initial water supply only need be on a relatively small percentage of the total outlets. As an example, in a public building having 400 hot water outlets, only 100 to 150 samples need be taken. Preferably, the samples would include any locations which could be defined as problem areas. These problems areas would include patient care and in particular, critical care areas in a hospital, areas under reconstruction, fixtures at the far end of the system which are potential stagnant areas, hot water storage tanks and return lines. The critical care and patient care areas are particularly important since it is necessary to ensure that no bacteria is in the water supply at those areas. Patients in those areas have reduced resistance to bacteria. Also areas under construction tend to have high bacteria levels.

Samples are initially analyzed for the level of Legionella bacteria in particular, and total bacteria in general. Further, corrosion indicators such as iron, zinc and copper are tested, to determine the level of corrosion within system 20. Water temperature is also tested.

Once the initial levels of bacteria are known, an initial chlorine level is determined. The higher the initial level of bacteria, the higher the chlorine level will be. Normally, chlorine levels of 7 to 10 parts per million will be adequate.

Then, a disinfection process begins. Chlorine is injected into system 20 at levels between 7 to 10 parts per million, depending on the degree of bacteria problem in system 20. A corrosion inhibiting material, which is preferably a sodium silicate blend, is set to 20 to 50 parts per million. Preferably, the sodium silicate is injected at a level not less than 3 times the level of chlorine being injected. The internal condition of the pipe prior to treatment determines the level of corrosion inhibitor required. If the distribution pipe is new or free from scale, the interior surfaces must be coated with the silicate inhibitor before the chlorine treatment is started, silicate levels of 50 parts per million should be used.

The disinfectant phase may require 5 to 7 weeks. Initially, the chlorine residual within the water must be maintained at 7 to 10 parts per million across the piping system. The chlorine level may be reduced after approximately a week from a high dosage level of 7 to 10 ppm to a more moderate level of 5 ppm. This disinfectant stage may include a first high dosage stage of approximately 10 parts per million for one week, then a more moderate dosage stage of 5 parts per million for approximately 5 weeks. Closely monitoring the test for Legionella bacteria and total bacteria will provide evidence of the chlorine level effectiveness. Alternatively, the levels will be adjusted based on the test data developed throughout the disinfectant phase. To protect the piping system against corrosion, the sodium silicate additive should be maintained at a minimum of 3 to 5 times the chlorine levels. Preferably, the sodium silicate is maintained at 4 times the level of chlorine. In a galvanized system, if the water becomes brown, one increases the silicate levels. The chlorine is preferably injected into line 30 at a time delay of approximately 4 seconds after the sodium silicate injection. This ensures that the corrosion inhibitor additive is in the water supply prior to chlorine injection.

Once injection begins, the combined chlorine and sodium silicate is drawn into storage tanks, through supply mains and into every water riser and outlet within the system. This continues until the chlorine level is tested between 7 and 10 parts per million within the water at every one of the building water outlet. If the water tested at any particular outlet does not have the desired level, the particular location is recorded for investigation and corrective action. Such corrective action would include attempts to increase water flow through that location, check the operation of the fixture, look for a cross-connector between the hot water and the cold water.

All hot water outlets are flushed during this period to ensure that they are all exposed to chlorine, and that bacteria will be eliminated. After the high dosage first week, the water will reach the desired chlorine level. Once this level has been stabilized throughout the system, the moderate dosage stage may be entered.

Samples continue to be taken from various outlets, although the percentage of samples may be reduced from the initial stage. As an example, should this moderate dosage stage continue for five weeks, 20 percent of the outlets could be tested each week. The samples are tested for the materials previously mentioned. It is desirable that the samples are rotated so that all outlets will be checked at least once during this period. It is desired to have final levels of zero Legionella and zero total bacteria at all outlets at the end of this stage.

During this stage, it is preferred that all outlets be flushed at least once a week to remove stagnate water and to flush out any organic debris. That would mean simply opening the outlets such that water flows out of them, and they are exposed to fresh chlorine. The problem areas described above should be flushed as much as twice a week during this phase. If the samples taken at the end of the moderate dosage stage are not as desired, the stage could be continued for additional weeks.

At the end of this stage, all outlets are tested. If the outlet water quality is as desired, then a maintenance phase may be entered. During the maintenance phase, a lower level of chlorine and corrosion inhibitor is maintained in the water supply system. The chlorine level may be reduced to 3.0 to 3.5 parts per million. The silicate level should be maintained at 25 parts per million, at least 4 times the chlorine level. Steps are taken to eliminate dead, stagnant and low flow areas. As an example, outlets which are seldom used are flushed occasionally to ensure that chlorine does flow through those outlet structures. Further, samples are periodically taken to ensure that the bacteria does not return.

FIG. 2 illustrates one system for adding additives to the water supply system. Additive system 34 includes hot water boiler 36 communicating with hot water tank 38 through line 40. Hot water tank 38 returns water to boiler 36 through line 44 and pump 46. Cold water makeup line 42 communicates with a source of cold water to ensure that the amount of water sent to hot water tank 38 from boiler 40 is sufficient. Return line 48 leads from the hot water supply system through pump 50, line 52, and line 44 to boiler 36.

A chlorine monitor 53 on line 52 monitors the amount of chlorine within return line 48. If the amount of chlorine is not as desired, a signal is sent through line 54 to chlorine injector 56 and line 57 to an corrosion inhibitor injector 58 to increase the supply of both additives to the water in makeup line 42. A main chlorine injector 61 and a main corrosion inhibitor injector 60 also supply additives to the water in makeup line 42.

A cold water supply 62 for the cold water makeup line 42 includes a direct line leading to cold water supply 42 and spur 64 leading through meter 66. Meter 66 controls chlorine injector 61, and injects an amount of chlorine proportional to the water passing into cold water makeup line 42. Meter 66 communicates through line 70 to the main corrosion inhibitor injector 60, which injects corrosion inhibitor additive into line 72. Line 72 communicates with outlet line 74 from hot water tank 38 leading to the hot water supply.

Since chlorine meter 53 monitors the amount of water in return line 48, and adds additional corrosion inhibitor material and chlorine to the line should that be necessary, it is ensured that the levels in the water are as desired. In a sense, chlorine monitor 53 acts as feedback to ensure that the desired amounts are maintained.

A second embodiment system 80 illustrated in FIG. 3 includes boiler 82 communicating with hot water tank 84 through supply line 86, and return line 88 leading through pump 90. Cold water makeup line 92 adds water to supply line 86. Return line 94 leads through pump 96 to line 98 which leads to line 88. Chlorine injector 100 leads through line 102 to cold water makeup line 92. Cold water supply line 104 leads to spur 106, which leads through meter 108. Line 110 controls the amount of chlorine sent into line 102. Line 112 leads to corrosion inhibitor injector 114, which controls the amount of corrosion inhibitor material sent to line 116 and to outlet 118 of hot water tank 84.

In a preferred embodiment of the present invention, the corrosion inhibitor material is a sodium silicate combination. A combination including 90.90% silicate of soda is combined with 4.953% water, and 2.73% caustic soda (78% $NA_2O$) and 0.757% sodium ash 58% $N_2O$ and 0.66% tri-sodium phosphate. In one example, 600 pounds of silicate soda available from PQ Corporation are added to 33 pounds of water, 18 pounds caustic soda available from Allied Chemical Company, 5 pounds of soda ash available from Allied Chemical Company, and 4 pounds of the tri-sodium phosphate available from Monsanto Company are used. This mixture is created by heating a vat and gradually dissolving the soda ash, the tri-sodium phosphate and the caustic soda into the hot water. Then, the silicate of soda is slowly added and the mixture simmers for 15 to 30 minutes. The mixture is then used as an corrosion inhibitor additive in the above described systems.

The injectors are all preferably electronic controlled injection pumps. One such pump is a diaphragm type pump incorporating an anti-syphen valve available from Dihydro Services, Inc. of Sterling Heights, Mich. The water meter is preferably an electronic pulse generating meter, which communicates with the injection pumps and give signals indicative of a desired amount of chlorine and corrosion inhibitor to be added to the water supply. Further, the chlorine monitor is of a known sort, and also sends electric signals to the injection pumps.

Preferred embodiments of the present invention have been disclosed, however, a worker of ordinary skill in the art would recognize that certain modifications would come within the scope of this invention. For that reason, the following claims should be studied in order to determine the true scope and content of this invention.

I claim:

1. A method of disinfecting a building water supply system of the type having a plurality of outlets comprising the steps of:
   (1) providing a water supply having a plurality of outlets, with said outlets receiving and dispensing both hot and cold water from hot and cold water supplies;
   (2) injecting chlorine into a hot water supply;
   (3) dispensing some of the hot water through outlets and returning some of the hot water through a hot water return line to the hot water supply, monitoring the hot water return line to monitor the amount of chlorine in that return line;
   (4) controlling the amount of chlorine injected into the hot water supply in response to the amount of chlorine in the return line to maintain the chlorine level at a desired level; and
   (5) injecting a corrosion inhibitor into the hot water supply in a controlled percentage relative to the chlorine during both steps (2) and (4).

2. The method recited in claim 1, wherein a first chlorine supply system injects chlorine to the water supply system, and a second chlorine supply system is actuated in response to the amount of chlorine monitored in the return line to add additional chlorine.

3. The method recited in claim 1 wherein the amount of corrosion inhibitor is controlled such that it is three times the amount of added chlorine.

4. The method recited in claim 1, wherein the chlorine is injected following a time delay after the injection of the corrosion inhibitor.

5. The method recited in claim 4, wherein the desired level of chlorine is intially determined by testing water samples from within the water supply system to determine the degree of the bacteria problem.

6. The method recited in claim 5, wherein chlorine levels are initially set at relatively high levels to initially disinfect the system, and a lower level maintenance dose of chlorine is maintained after the initial high levels.

7. The method recited in claim 6, wherein the initial high level treatment includes testing the water from a percentage of the water outlets of the system periodically.

8. The method recited in claim 7, wherein the method also includes the steps of identifying problem outlet areas which require more frequent testing than other system outlets, and testing said problem outlet areas more frequently than said other system outlets.

9. The method recited in claim 3, wherein the level of chlorine injected into the water is 7 to 10 parts per million.

10. The method recited in claim 9, wherein the level of corrosion inhibitors is three times that of the chlorine.

11. A method of disinfecting water in a hot water supply of a building comprising the steps of:
   (1) initially testing various outlets in the water supply systems to determine the degree of bacteria problem within the hot water supply system;
   (2) identifying a desired level of chlorine to effectively disinfect the bacteria in the hot water supply system, the level of chlorine being determined by the level of bacteria in the water supply system;

(3) initially injecting a first high quantity of chlorine into the water supply system for a first period of time;

(4) monitoring and flushing outlets within the water supply system such that all outlet portions of the water supply system are exposed to the chlorine;

(5) maintaining a lower chlorine level in the water supply system after the first period of time; and (6) monitoring the level of chlorine in the lines and insuring that the level of chlorine is maintained as desired during both steps (3) and (5); and (7) injecting a corrosion inhibitor material into the system along with the chlorine during both steps (3) and (5).

12. The method recited in claim 11, wherein the first high quantity is set to be at least twice the lower chlorine level.

* * * * *